United States Patent
Swanson et al.

(10) Patent No.: US 6,219,138 B1
(45) Date of Patent: Apr. 17, 2001

(54) PARTICLE SIZING TECHNIQUE

(75) Inventors: Nancy L. Swanson, Newburg, MD (US); Barton D. Billard, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/480,535

(22) Filed: Jan. 10, 2000

(51) Int. Cl.$^7$ .................................................. G01N 15/02
(52) U.S. Cl. ............................................. 356/336; 250/575
(58) Field of Search ..................................... 356/335, 336, 356/337, 338, 339, 340, 341, 342, 343; 250/574, 575

(56) References Cited

U.S. PATENT DOCUMENTS

| | | | |
|---|---|---|---|
| 3,310,946 | 3/1967 | Dobbins | 60/219 |
| 4,015,135 | 3/1977 | Tipton, Jr. | 250/574 |
| 4,245,909 | 1/1981 | Loos | 356/336 |
| 4,361,403 | 11/1982 | Loos | 356/336 |
| 4,497,577 | * 2/1985 | Sato et al. | 356/336 |
| 4,565,448 | * 1/1986 | Abbott et al. | 356/339 |
| 4,801,205 | 1/1989 | Tatsuno | 356/336 |
| 4,928,153 | * 5/1990 | Glass | 356/343 |
| 5,090,808 | * 2/1992 | Ishikawa et al. | 356/336 |
| 5,164,787 | 11/1992 | Igushi et al. | 356/336 |
| 5,309,216 | * 5/1994 | Weichert | 356/335 |
| 5,571,855 | 11/1996 | Palmer et al. | 524/432 |
| 5,619,324 | * 4/1997 | Harvill et al. | 356/336 |
| 5,793,478 | 8/1998 | Rader et al. | 356/28 |
| 5,818,583 | * 10/1998 | Sevick-Muraca et al. | 356/336 |

OTHER PUBLICATIONS

Dobbins, Richard A. and Jizmagian, G. Stephen, "Particle Size Measurements Based on Use of Mean Scattering Cross Sections"; Oct., 1966; Journal of the Optical Society of America, vol. 56, No. 10; pp. 1351–1354.

Dobbins, Richard A. and Jizmagian, G. Stephen, "Optical Scattering Cross Sections for Polydispersions of Dielectric Spheres"; Oct., 1966; Journal of the Optical Society of America, vol. 56 No. 10; pp. 1345–1350.

* cited by examiner

*Primary Examiner*—Hoa Q. Pham
*Assistant Examiner*—Sang H. Nguyen
(74) *Attorney, Agent, or Firm*—James B. Bechtel, Esq.; Wyatt B. Pratt, Esq.

(57) ABSTRACT

The particle size within a given medium is determined using a single wavelength to confirm the known particles sizes within a dispersion, or determined from two wavelengths to calculate the unknown particle sizes of a dispersion. Three wavelengths may be used to determine the unknown particle size of a dispersion of unknown concentration within a medium. The method and apparatus may be used for mono-dispersions and poly-dispersions.

43 Claims, 4 Drawing Sheets

PARTICLE SIZING TECHNIQUE

BACKGROUND OF THE INVENTION

1. Field of the Invention

The present invention relates to a method and apparatus for determining a particle size within a given medium. More particularly, the particle size may be determined using a single wavelength to confirm a known particle size within a dispersion, or determined using two wavelengths to calculate an unknown particle size within a dispersion. Three wavelengths may be used to determine an unknown particle size within a dispersion with unknown concentration. The method and apparatus may be used for mono-dispersions and poly-dispersions.

2. Brief Description of the Related Art

As monochromatic light traverses a random, attenuating medium, the radiant intensity decays exponentially with path length and attenuation coefficient. This relationship was first formulated by Pierre Bouguer (1698–1758). Many authors also credit Lambert for deriving this relation. When the attenuation is expressed in terms of the particle concentration, the formula for exponential decay is known as Beer's Law. Beer's law was used to determine the concentration of an absorbing substance by comparing to a standard substance of known concentration. The exponential decay law has thus been called the Bouguer, Lambert, or Beer Law, or some hyphenated combination of these three, herein referred to as the Bouguer-Lambert-Beer Law, or the BLB law.

Considerable confusion exists regarding the applicability limits of the Bouguer-Lambert-Beer Law of optical transmission. The BLB law can be derived directly from conservation of energy considerations. As such, it is a heuristic law. It also can be derived, under certain simplifying assumptions, as a solution to the radiative transport equation (RTE), which is itself a heuristic formula.

Light traversing a random medium is attenuated by both scattering and absorption. It is well known that radiant intensity measured after the light traverses the medium cannot include any scattered light. For this reason, the BLB law has often been called the BLB law of optical absorption. It has been generally assumed that the BLB law is valid only when scattering is negligible. Some authors have recognized the applicability of the BLB law to optically dense media, provided the scattered light is appropriately filtered. Several articles have heretofore stated that the BLB law was an approximation, because the scattered light cannot practically be excluded.

Several methods are known for determining the mean size in a sample of particles. One method includes scanning the sample with an electron microscope, and processing the resulting image, either by hand or with image processing software, to determine the mean size of the particles within the image.

A second method, described in *Absorption and scattering of light by small particles*, by Bohren and Huffman, Wiley and Sons, 1983, Section 11.17, measures the extinction, i.e., optical thickness, as a function of wavelength which is compared to curves calculated from the Mie theory. This requires a spectrophotometer capable of making measurements over a large range of wavelengths, as well as a library of extinction curves, generated from the Mie theory over the same wavelength range, for many different sizes and refractive indices. The measured curve is compared to the curves in the library and the curve that best matches the data is chosen as a mean size of the particles in the sample.

The third method measures scattered intensity at a given angle, usually 90 degrees, with the incident intensity known. A lookup table is prepared for the expected measured intensity at that angle over a range of sizes at a specific refractive index ratio. The values in the table are generated from the Mie theory. The measured intensity is compared to the values in the table. The closest match corresponds to the mean size of particles in the sample.

The fourth method, described in "Determination of soot parameters by a two-angle scattering-extinction technique in an ethylene diffusion flame," by De Iuliis et al., Appl. Opt., vol. 37, no. 33, p. 7865, 1998, measures the extinction as in the second described method at a single wavelength. The scattering is assumed negligible and the attenuation is due only to absorption. This requires a very dilute sample and a laser wavelength for which the particles are strongly absorbing. Thus, for sampling many different types of materials, a frequency agile laser or multiple lasers is required. The absorption coefficient is proportional to the cube of the particle size. Measurement of the extinction yields the absorption, which yields the mean particle size in the sample.

A fifth method measures the Doppler shift in the scattered light. For particles suspended in fluid heterodyne detection methods are required since the frequency shift is small. This method requires a complicated setup and data analysis. The line width of the scattered spectrum is proportional to the diffusion coefficient, which is inversely proportional to the particle size.

Accordingly, there is a need in the art to provide a method and apparatus to apply the BLB law for scattering media with increased concentrations, and without the necessity of generating and comparing libraries of curves.

SUMMARY OF THE INVENTION

The present invention comprises a method of determining particle sizes using the BLB law in the presence of significant scattering that includes two primary methods, and variations thereof, for determining particle size. In one method the steps include: measuring optical transmission of a sample containing a dispersion of the particles within a medium relative to the transmission of the medium alone; calculating the optical thickness $\tau$ from the measurement; measuring the ratio of volume of particles to volume of the dispersion R; generating the extinction Q as a function of size parameter x for the wavelength used in the measurement of $\tau$, calculating the predicted ratio of the volume of particles to volume of the dispersion as a function of size parameter x from Q and the measured $\tau$, comparing the measured volume ratio R to the predicted volume ratio by graphical means; and finding all values of size parameter x where the measured volume ratio R matches the predicted volume ratio. A known particle size is confirmed if it is consistent with the size parameter where one of the matches occurs.

In a second method the steps include: measuring optical transmission of a sample containing a dispersion of the particles within a medium relative to the transmission of the medium alone; calculating the optical thickness $\tau$ from the measurement; measuring the ratio of volume of particles to volume of the dispersion; generating the extinction Q as a function of size parameter x for the wavelength used in the measurement of $\tau$, calculating the predicted optical thickness $\tau$ as a function of size parameter x from Q and the measured R; comparing the measured optical thickness $\tau$ to the predicted optical thickness by graphical means; and finding all values of size parameter x where the measured optical thickness τ matches the predicted optical thickness. A known particle size is confirmed if it is consistent with the size parameter where one of the matches occurs.

Variations on these methods are made when the particle size is unknown, when both the particle size and the concentration is unknown or it is impractical to measure the concentration, and when the particles have a distribution of sizes (polydispersion instead of monodispersion) and the mean size is to be measured.

DETAILED DESCRIPTION OF THE PREFERRED EMBODIMENT

The present invention provides a method and apparatus for determining a particle size within a given scattering medium. The particle size may be determined from measurements made using a single wavelength to confirm a known particle size within a dispersion, or from measurements made using two wavelengths to determine an unknown particle size within a dispersion. Additionally, three wavelengths may be used to determine the particle size of a mixture within a medium of unknown concentration. The method and apparatus may be used for monodispersions and poly-dispersions to quickly and easily determine a previously unknown mean size of particles or verify a previously known mean size of particles in a given sample.

First Step Both Methods

Figure 1A:
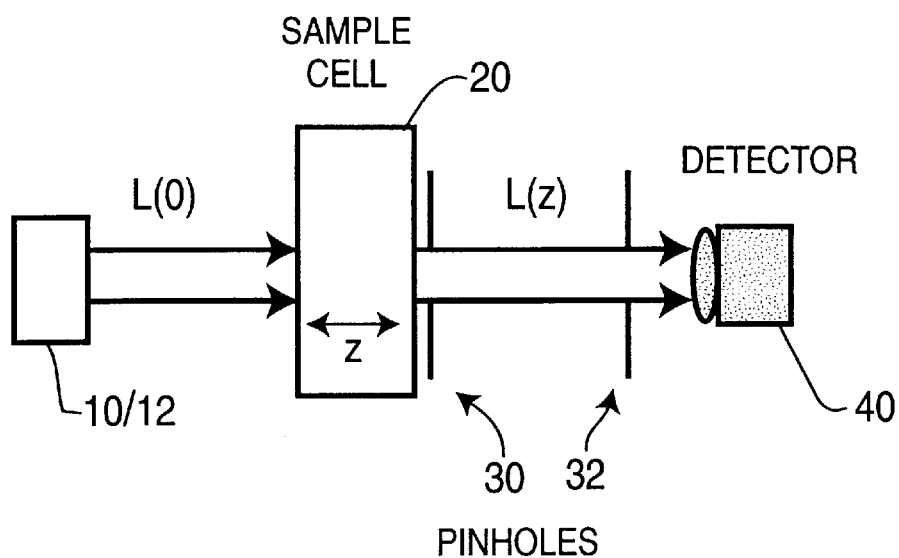
FIGS. 1A and 1B show a schematic of the experimental setup for measuring optical thickness τ of a sample solution.
Figure 1B:
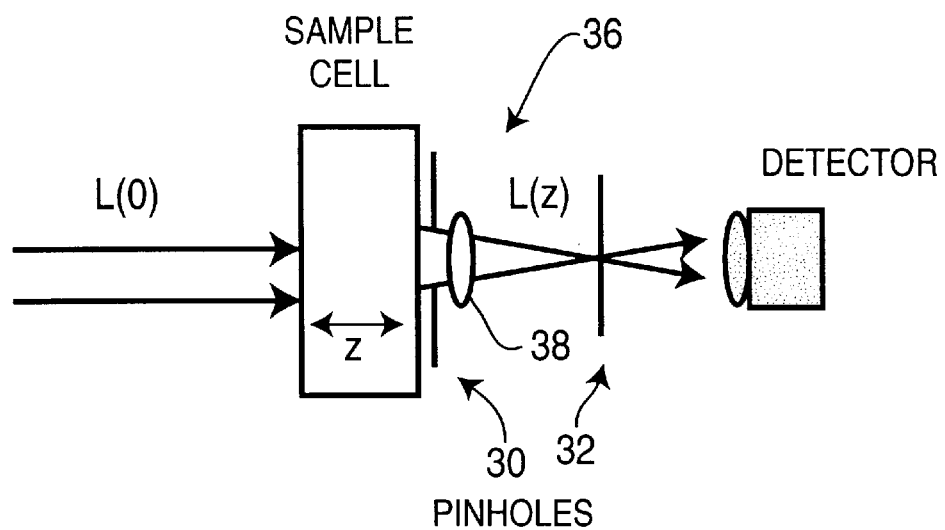

Referring to FIGS. 1A and 1B, schematics of the experimental setup for measuring optical thickness τ of a sample solution are shown. As seen in FIG. 1A, a monochromatic, collimated electromagnetic radiation source 10, such as a laser, is used. Two pinholes 30 and 32 are aligned between a sample cell 20 and the laser 10, with the first pinhole 30 adjacent to the sample cell 20 and the second pinhole 32 adjacent to a linear response detector 40. The second pinhole 32 serves to reject scattered light that exits the sample cell 20 at an angle greater than the half angle $\theta_{1/2}$, referred to as the half angle of acceptance, subtended by the second pinhole 32 at points within the opening of the pinhole 30. The sample cell 20 comprises a solid dispersed in a medium, such as water. If particles off the beam axis are illuminated by scattered light, that light can be scattered toward the detector 40. The first pinhole 30 adjacent to the sample cell 20 limits this multiply scattered light.

The pinholes 30 and 32 are sufficient for screening the scattered light for the particle sizes that are comparable to the wavelength of the laser 12. For particles that are very large compared to the wavelength, however, a lens-pinhole system 36 becomes required, as shown in FIG. 1B. In place of the first 30 and second 32 pinholes, the lens-pinhole system 36 comprises a lens 38 mounted between the two pinholes 30 and 32. The lens 38 provides an alteration of the radiation from the laser 12 after passing through the sample cell 20, which focuses the transmitted light. Any scattered light does not focus, thus the pinhole 32 placed at the focal length of the lens blocks the scattered component. The BLB law may be accurately applied, even in the presence of significant multiple scattering, provided that the measuring apparatus is correctly constructed. For very large diameter particles relative to the wavelength, such as when the ratio d/λ is about 20 or greater, a lens as shown in FIG. 1B is used.

Best results are attained when the pinholes 30 and 32 are such that the half angle of acceptance $\theta_{1/2}$ is $\theta_{1/2} \leq 5°\lambda/d$, with λ being the wavelength in the medium, to provide adequate accuracy for measurements, with the proper half angle being determinable by those skilled in the art.

The optical thickness τ results from the equation $L(z)=L(0)^{-\xi z}$, wherein L(z) and L(0) are intensities measured with a linear response photodetector, z is the optical path length in the medium and $\xi=\xi_s+\xi_a$ is the total attenuation coefficient (absorption+scattering). The optical thickness of the sample solution is determined by measuring the intensities of an electromagnetic source with and without the sample solution in the beam path of the electromagnetic source. Measurements are taken from a clear filtered medium, such as water with no particles, with successive measurements made after adding known amounts of a solid component. The effects of the medium and the surfaces of the sample cell are canceled in the equation $L(z)=L(0)e^{-\tau}$ by using the measurement obtained from the filtered medium for L(0), assuming those effects are multiplicative. By knowing the particle density and carefully measuring the dilutions, the particle density at each measurement of optical thickness is known.

Figure 2:
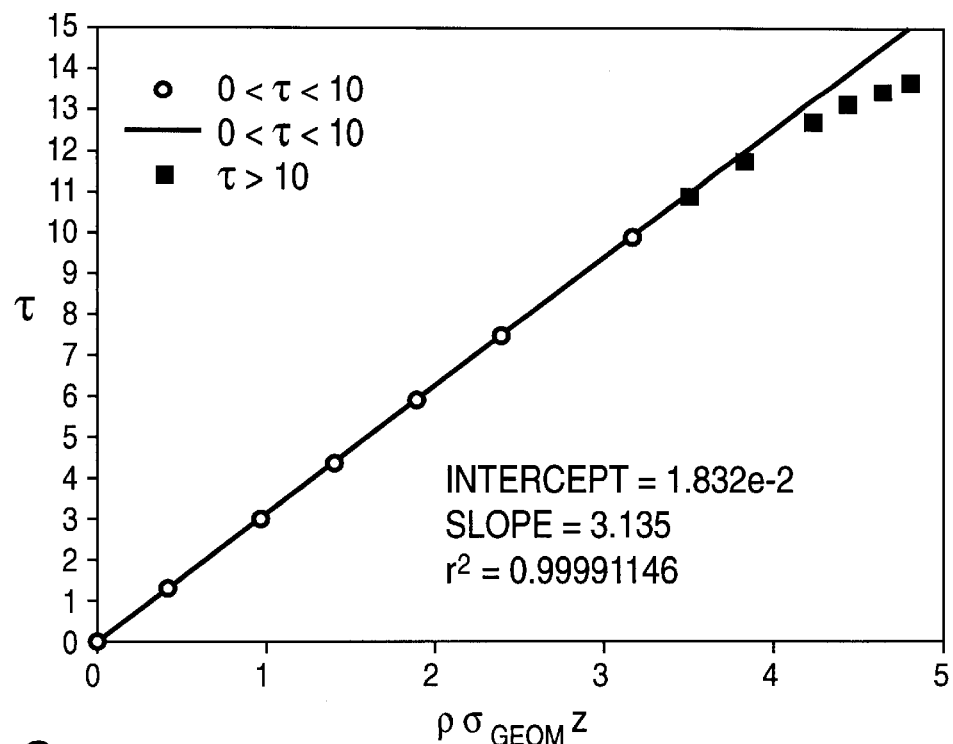
FIG. 2 is a plot of the measured τ vs. particle concentration for 1.0 µm spheres.
Figure 3:
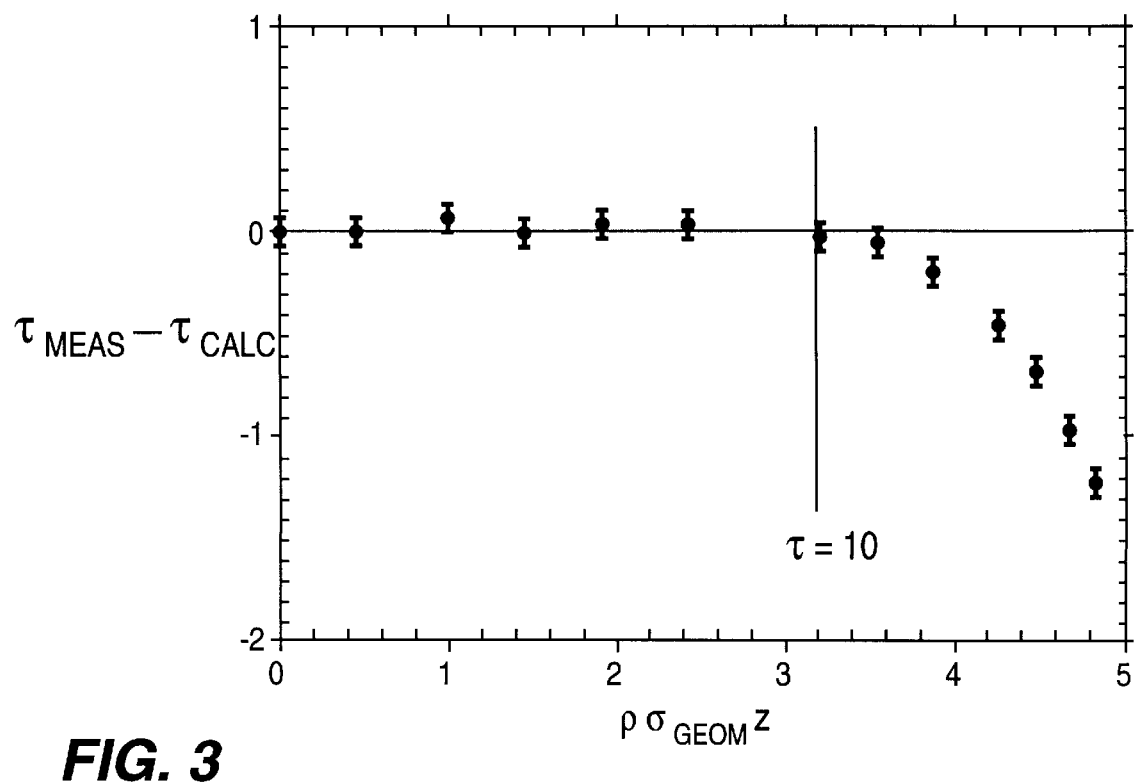
FIG. 3 is a plot of the calculated τ minus measured τ vs. particle concentration.

As a test of the applicability of the BLB law using the approach of FIG. 1 in the presence of significant multiple scattering, the following analysis of the data was performed. The optical thickness τ is a product of the total attenuation ξ times the optical path length z. The attenuation ξ is the product of the particle number density ρ times the total cross section σ, therefore optical thickness τ can be written as τ=ξz=ρσz. With the scattering efficiency, called the Mie extinction parameter Q given by $Q=\sigma/\sigma_{geom}$, where $\sigma_{geom}$ is the geometric cross section, the optical thickness is $\tau=Q\rho\sigma_{geom}z$. As seen in FIG. 2, a plot of τ as a function of $\rho\sigma_{geom}z$, results in a line with slope equal to Q in the region τ where the BLB law is valid. When the data begin to deviate from the line, application of the BLB law is no longer reliable. FIG. 2 shows data for d=1.0 µm, with the slopes, intercept and $r^2$ values having the best linear fit for $0<\tau\leq 9.95$. The slope as shown in FIG. 2 is the extinction Q=3.135±0.094; the extinction calculated from the Mie theory is $Q_{Mie}=3.151$. FIG. 3 shows the same data plotted as the difference between the measured τ and τ calculated from the equation $\tau=Q\rho\sigma_{geom}z$ using for Q the best fit slope of the linear portion of the plot in FIG. 2. In FIG. 3, the measured τ diverges from the calculated value of τ for concentrations resulting in τ>10.

Measuring the ratio R of volume of particles to volume of the dispersion comprises using the relationship of R=s/δ, where s is the fraction of solids (in mass per unit volume of sample solution) corresponding to a measured value of τ, and δ is the density of the particles is the fraction of solids (in mass per unit volume). The sample dilution is prepared and the ratio of solids s is calculated based on the dilution.

A curve from Mie theory for Q as a function of the size parameter x, defined as x=πd/λ, where d is the diameter of the sphere is generated. Q may be determined numerically from a computer program implementation of the Mie theory using the size parameter and the refractive index ratio m, particle to medium, as inputs.

First Method Final Steps (Predict R For Constant $\tau$, Verify Known Size)

The predicted volume fraction ratio may be generated from a determined value generated from the Mie theory output Q(x). The relationship is given by $R(x)=2\lambda\tau x/3\pi zQ(x)$, wherein R is the predicted volume fraction occupied by the solids in the sample solution, $\lambda$ is the wavelength of the radiation in the medium, $\tau$ is the optical thickness of the sample, x is size parameter, z is the optical path length, and Q is the scattering efficiency. Common values of the predicted volume fraction ratio and the measured value of R are determined by plotting R(x) as a function of x. Once plotted, a constant line at the measured value of R is extended through the plot to correlate all common values. Common values of the predicted volume fraction ratio and the measured value of R are determined with at least one determined common value representing the particle size of the solids within the sample solution. A known particle size is confirmed if it is consistent with the size parameter where one of the common values of measured and predicted R occurs.

Second Method Final Steps (Predict $\tau$ For Constant R, Verify Known Size)

Additionally, the particle sizing technique of the present invention comprises predicting the optical thickness as a function of size parameter x instead of predicting the volume fraction ratio. The predicted optical thickness $\tau$ is given by the equation $\tau(x)=3\pi zRQ(x)2\lambda x$, wherein z is the optical path length, R is the volume fraction, Q is the scattering efficiency, x is the size parameter equal to $\pi d/\lambda$, with d the sphere diameter, and $\lambda$ is the wavelength. Common values of the predicted optical thickness and the measured value of $\tau$ are determined by plotting $\tau(x)$ as a function of x. Once plotted, a constant line at the measured value of $\tau$ is extended through the plot to correlate all common values. A known particle size is confirmed if it is consistent with the size parameter where one of the common values of measured and predicted R occurs.

With either method, the volume fraction or the optical thickness, a confirmed particle size measurement of a sample of particles of known size is obtained by the use of a single wavelength. This provides a method of quality control for a known sample. The parameters of the ratio of solids s, the particle material density $\delta$, and the refractive indices of the particles and medium, at the probe wavelength, need to be known or measured, with the total number of measurements being three: the dilution and the intensity before and after placing the sample in the beam path.

Variation of Methods for Unknown Particle Size

If the particle size is unknown, the two methods are modified to use measurements at two wavelengths. Alternatively, the solids may be suspended in two media having different refractive indices and measurements at the same wavelength taken with each suspension.

Variation of First Method for Unknown Particle Size

For the variation of the First Method, two curves representing the predicted R must be generated, and measurements must be made. Conditions must be varied between the two measurements to sufficiently separate the two curves, for example by making the measurements at two wavelengths. If the refractive index of the particles and medium are the same for both wavelengths, then the curves of R(x) can be separated by converting to R(d) at each wavelength. An alternative method suspends the solids in two different solutions that have very different refractive indices. Two curves of Q(x) are generated, one for each refractive index ratio. Measurements are then made at a single wavelength for each of the two dispersions.

For each of the measurements, the predicted volume ratio is expressed in terms of Q(d) and the optical thickness of the sample, and then plotted as a function of diameter d instead of size parameter x. The predicted volume fraction ratio as a function of d is generated by the equation $R(d)=2\tau d/3zQ(d)$, with $\tau$ being the optical thickness, z the optical path length, R(d) the predicted volume fraction, Q(d) the scattering efficiency, $\lambda$ the wavelength in the medium, and d the sphere diameter. Computationally, it is convenient for $\tau$ to be held constant, which may be accomplished with the addition of medium or solids between measurements at the two wavelengths. When operationally $\tau$ can not be held constant, i.e., smoke plumes, then R must be recalculated for both measured $\tau$s. The measured value of R is then superimposed on the plot. The intersections of the constant, measured value of R with the curve of the predicted volume ratio versus d give corresponding diameters. The ambiguity of the first measured value of R intersecting more than once with the corresponding curve of predicted volume ratio is resolved by the second combination of measurement and prediction. The second measured value of R is superimposed over a second plot of predicted volume ratio versus d at the second wavelength or using the second refractive index ratio, providing a unique value of d corresponding to both measured values of R. If the refractive index of either the particle or the medium is different as a result of changing the wavelength or using a second medium, a second generated curve of Q versus x would be needed to calculate the new predicted volume ratio for the new refractive index ratio.

Variation of Second Method for Unknown Particle Size

For the variation of the Second Method, two curves representing the predicted optical thickness $\tau$ must be generated., and two measurements must be made. Conditions must be varied between the two measurements to sufficiently separate the two curves, for example by making the measurements at two wavelengths. If the refractive index of the particles and medium are the same for both wavelengths, then the curves of $\tau(x)$ can be separated by converting to $\tau(d)$ at each wavelength. An alternative method would be to suspend the solids in two different solutions that have very different refractive indices. Two curves of Q(x) are generated, one for each refractive index ratio. Measurements are then made at a single wavelength for each of the two dispersions.

For each of the measurements the optical thickness is expressed in terms of Q and the measured volume fraction ratio occupied by the spheres, and then plotted as a function of d. The predicted optical thickness $\tau$ as a function of d is generated by the equation $\tau(d)=3zQ(d)/2Rd$, with R being the measured volume fraction ratio, z the optical path length, Q(d) the scattering efficiency, $\lambda$ the wavelength in the medium, and d the sphere diameter. The measurement of $\tau$ for a known particle concentration is then superimposed on the plot. The intersections of the constant, measured value of τ with the curve of predicted optical thickness versus d give the corresponding mean diameters. The ambiguity of the first measured τ intersecting more than once with the curve of predicted optical thickness is resolved by the second combination of measurement and prediction. The second measured value of τ is superimposed over a second plot of predicted optical thickness versus d at the second wavelength or using the second refractive index ratio, providing a unique value of d corresponding to both measured values of τ. With the second method it is not necessary to change the concentration of the sample, since both computationally and experimentally it is most convenient to maintain a constant concentration. If the refractive index of either the particle or the medium is different as a result of changing the wavelength or medium, a second generated plot of Q versus x would be needed to calculate the predicted optical thickness for the new refractive index ratio. As seen in FIGS. 4A–4B and 5A–5B, the particle sizing technique of the present invention includes the use of two wavelengths to determine the particle size of an unknown particle.

Variation For Polydispersions

Poly-dispersions may be calculated by determining the particle radius as a volume-surface mean radius. As such, the particle radius $r_{32}$ is defined as:

$$r_{32} = \frac{\int_0^\infty N(r)r^3 dr}{\int_0^\infty N(r)r^2 dr}$$

with N(r) being the size distribution function. The scattering efficiency Q becomes a mean value $Q(r_{32})$ defined by the equation:

$$Q(r_{32}) = \frac{\int_0^\infty Q(r,m)N(r)r^2 dr}{\int_0^\infty N(r)r^2 dr}.$$

Variation for Unknown Size and Concentration

Three wavelengths may be used to determine the particle size for an unknown concentration of solids in the sample solution. The technique with three wavelengths comprises comparing two or more of the ratios of:

$\tau(\lambda_1)/\tau(\lambda_2) = Q(\lambda_1,d)/Q(\lambda_2,d)$;

$\tau(\lambda_1)/\tau(\lambda_3) = Q(\lambda_1,d)/Q(\lambda_3,d)$;

and $\tau(\lambda_3)/\tau(\lambda_2) = Q(\lambda_3,d)/Q(\lambda_2,d)$;

with $\lambda_1$ being the first, $\lambda_2$ being the second and $\lambda_3$ being the third wavelengths and τ being the optical thickness at the first, second or third wavelength. The concentration is kept fixed for the three measurements, so that the volume ratio cancels when taking the ratio. The two or more ratios at three wavelengths are plotted as a function of d for comparison. The ratios are compared, as predicted values, to the ratios of the measured values of optical thickness at the corresponding wavelengths, made with a fixed volume ratio for the sample.

EXAMPLE 1

Determining the Unknown Particle Size of a Sample

The following procedure was used to determine the unknown size in a liquid suspension. Polystyrene spheres were suspended in water that was filtered through a 0.2 μm filter. A Texas Instruments TSL 230 chip detector was used to convert incident irradiance to output frequency through a silicon photodiode and a current-to-frequency converter. The detector response was linear over six orders of magnitude, with the linear response verified by calibrating the detector with a radiometer and neutral density filters. A National Instruments Data Acquisition (DAQ) card was programmed as a frequency counter. For each data point, the frequency was counted 50 times, and the mean and standard deviation of the mean were saved to a data file. The output frequency was verified with both a frequency counter and an oscilloscope.

The experimental setup was arranged as previously described for the schematic of FIG. 1A. A 30 mW argon-ion laser, operating at the 514.5 nm line, was used. The pinhole adjacent to the detector served to reject scattered light that exited the sample cell at an angle greater than the half angle subtended by the pinhole at the same cell of $\theta_{1/2}$. Particles off the beam axis, illuminated by scattered light, were scattered toward the detector. The pinholes were approximately 1 mm in diameter. The half angle of acceptance was 0.3°, which resulted in a solid angle of $8.6 \times 10^{-5}$ steradians. It was found that a half angle of $\theta_{1/2} \leq 8°\lambda/d$, with λ the wavelength in the medium, was adequate for measurements up to d=10 μm. The largest particle used for the experiment was 9.67 μm at a minimum wavelength of 488 nm, yielding $\theta_{1/2}=0.303$, which was greater than the acceptance angle of 0.3°. The optical thickness was measured from the equation $L(z)=L(0)e^{-\xi z}$.

Measurements were taken with clear, filtered water containing no particles, followed by successive measurements while adding known amounts of polystyrene spheres. The effects of the water and the glass surfaces are canceled from the equation $L(z)=L(0)e^{-\xi z}$ by using the measurement for filtered water for I(0), assuming those effects were multiplicative. The particle density was given by the manufacturer in terms of the percent solids. With careful measurement of the dilutions, the particle density at each measurement of τ was known. The optical path length was 2.4 cm.

Figure 4B:
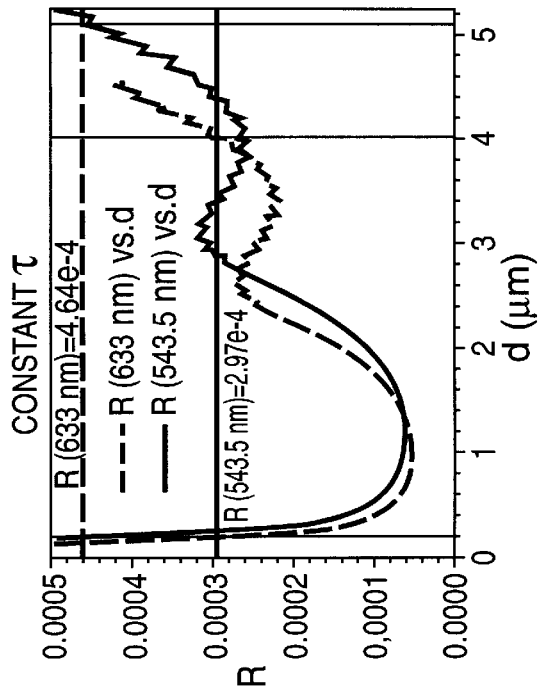
FIGS. 4A and 4B show plots of the results of particle sizing technique for d=0.202±0.006 µm, actual size.
Figure 5B:
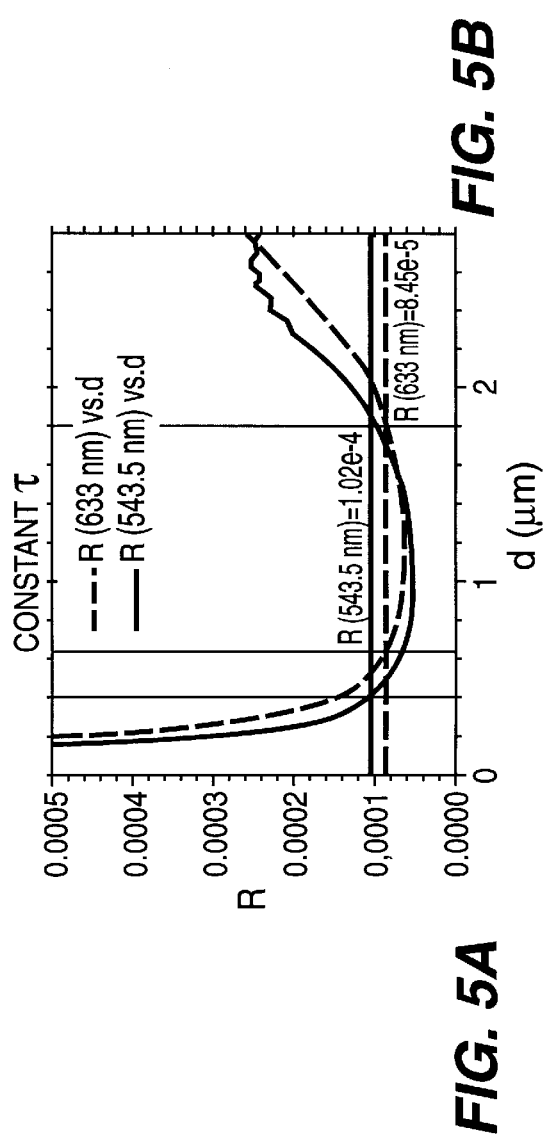
FIGS. 5A and show plots of the results of particle size technique for d=1.771±0.028 µm spheres; and, FIG. 6 is shows a plot of the ratio of optical thickness at two wavelengths as a function of particle size.
Figure 4A:
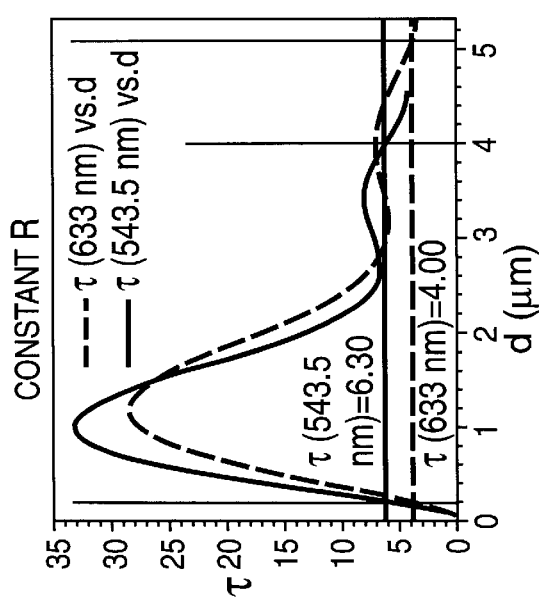
Figure 5A:
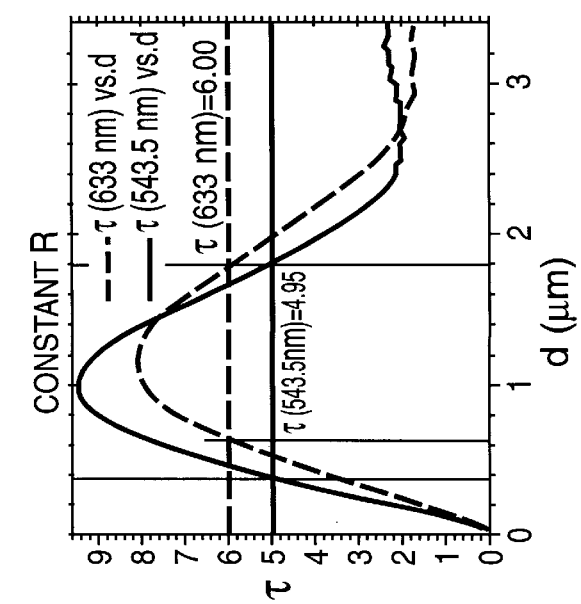

The values for the functions Q(x) were determined numerically from a FORTRAN implementation of the Mie theory using the refractive index ratio m (particle to medium) as input. Two curves $Q_1$ and $Q_2$ were generated by converting the x-axis from the size parameter to d, the sphere diameter, which separated out the two wavelengths. The corresponding two curves for the volume fraction ratios $R_1$ and $R_2$ were generated using $R(d)=2\tau d/3zQ(d)$. The measured value of R from R=s/δ, at constant τ, was plotted for both wavelengths. The volume fraction R versus sphere diameter for polystyrene in water was plotted at two wavelengths: 514.5 nm (Argon ion laser) and 633 nm (HeNe laser). Equivalently, the curves were generated for τ(d) using $\tau(d)=3zRQ(d)/2d$. Sample curves for R(d) and τ(d) are shown in FIGS. 4 and 5. FIGS. 4A and 4B show plots of the results of particle sizing technique for d=0.202±0.006 μm, actual size, with possible values for 633 nm at 0.20 and 5.08 μm, and possible values for 543.5 nm at 0.20 and 4.01 μm. The measured value is d=0.20±0.02 μm. FIGS. 5A and 5B show plots of the results of particle size technique for d=1.771±0.028 μm spheres with possible values for 633 mn at 0.64 and 1.80 μm. The measured value is d=1.80×0.09 μm.

The stated actual sizes were provided from the manufacturer's transmission electron microscope analyses. Results for all data, using the method of keeping R constant, are shown in Table 2, below.

As seen in Table 2, the second and third columns show possible values for d, representing the number of times the measured value of τ intersected the curve. The measured diameter remained unresolved for the 3.36 μm spheres because the two curves are not sufficiently separated for at the 3.36 μm size. The large number of possible diameters for the larger spheres results from small oscillations, called whispering gallery modes, causing many interceptions of the measured and theoretical values. The largest error occurs in the measurement for R, resulting from a rather large error in percent solids given by the manufacturer, which are compounded by sample dilutions. Typical errors range from about 1.2% or less. This error may be minimized by weighing a sample wet and dry to obtain the percent solids.

The method of the present invention determines particle size with only two measurements of τ, generally for values of 0<τ<10. Additionally, a single measurement at one wavelength is sufficient for particles known to be small, which covers only the monotonically increasing portion of the curve, between 0–1 μm for polystyrene in water.

the curve for R (or τ). The intersection of the curve with the measured value gives the possible values of the diameter. There will be more than one diameter that matches, but since the particle size is already known, the known value is thus verified.

EXAMPLE 3

Determining the Unknown Particle Size from a Sample of Unknown Concentration

In Example 1, the measured particle size for the 3.36 μm particles was undetermined. This was chosen as an example of the ratio method. The experiment was repeated for the 3.36 μm particles, replacing the 543.5 nm helium-neon laser with the 488 nm line of an argon-ion laser to give the maximum frequency separation possible in the visible spectrum. The data are presented in Table 3, below. The mea-

TABLE 2

| d (μm) M/F* | d (μm) 633 nm | d (μm) 543.5 nm | d (μm) measured | τ 633 nm | τ 543.5 nm | R(× $10^{-4}$) |
|---|---|---|---|---|---|---|
| 0.202 ± .006 | 0.20 ± .01 5.08 ± .22 | 0.20 ± .01 4.01 ± .17 | 0.20 ± .01 | 4.02 ± .02 | 6.30 ± .01 | 2.97 ± .16 |
| 0.629 ± .012 | 0.68 ± .07 1.73 ± .22 | 0.69 ± .07 1.34 ± .13 | 0.69 ± .07 | 2.35 ± .02 | 3.10 ± .01 | .031 ± .03 |
| 1.007 ± .024 | 0.93 ± .04 1.42 ± .06 | 0.97 ± .04 | 0.95 ± .04 | 4.90 ± .01 | 6.02 ± .01 | 0.54 ± .02 |
| 1.418 ± .042 | 0.95 ± .06 1.38 ± .08 | 0.64 ± .04 1.40 ± .08 | 1.39 ± .08 | 6.39 ± .02 | 6.46 ± .02 | 0.69 ± .04 |
| 1.771 ± .028 | 0.64 ± .01 1.80 ± .04 | 0.40 ± .01 1.80 ± .04 | 1.80 ± .04 | 6.00 ± .02 | 4.95 ± .02 | 0.85 ± .01 |
| 2.445 ± .081 | 0.33 ± .01 2.49 ± .09 | 0.23 ± .01 2.45 ± .09 | 2.47 ± .09 | 6.03 ± .02 | 4.95 ± .02 | 1.94 ± .06 |
| 3.36 ± .11 | 0.26 ± .02 2.92 ± .17 3.00 ± .18 3.26 ± .19 3.32 ± .20 3.36 ± .20 4.46 ± .26 4.49 ± .26 | 0.24 ± .01 2.33 ± .13 3.40 ± .19 | Not determined 0.25 ± .02 or 3.38 ± .20 | 4.62 ± .02 | 6.30 ± .02 | 2.23 ± .12 |
| 3.92 ± .14 | 0.27 ± .01 2.76 ± .13 3.66 ± .18 3.74 ± .18 4.02 ± .19 4.14 ± .20 4.23 ± .20 | 0.20 ± .01 4.00 ± .20 | 4.01 ± .20 | 6.08 ± .02 | 5.63 ± .02 | 2.60 ± .11 |

M/F* Indicates size as specified by the manufacturer

EXAMPLE 2

Determining the Known Particle Size of a Sample

The procedure for verifying a known particles size is similar to that for the unknown size. In this case only one curve is generated for R (or τ) and one measurement made. The measured value of either R (or τ) is plotted along with sured diameter for the 3.36 μm particles remains unresolved, however, the size of 0.25 μm was eliminated and 3.17 μm was added as a possible d. Because the 3.17 μm possibility did not appear in the first test, it is assumed that the diameter is about 3.3 μm, the average of the two measurements in Tables 2 and 3.

TABLE 3

| d (μm) M/F* | d (μm) 633 nm | d (μm) 488 nm | d (μm) measured | τ 633 nm | τ 488 nm | R(× $10^{-4}$) |
|---|---|---|---|---|---|---|
| 3.36 ± .11 | 0.25 ± .01 2.95 ± .15 3.03 ± .16 3.16 ± .16 3.24 ± .17 4.51 ± .23 | 0.21 ± .01 2.13 ± .11 2.82 ± .14 2.89 ± .14 3.18 ± .16 3.24 ± .16 | Undeter. 3.17 ± .16 or 3.24 ± .17 | 4.07 ± .03 | 6.00 ± .02 | 1.99 ± .09 |

M/F* Indicates size as specified by the manufacturer

Figure 6:
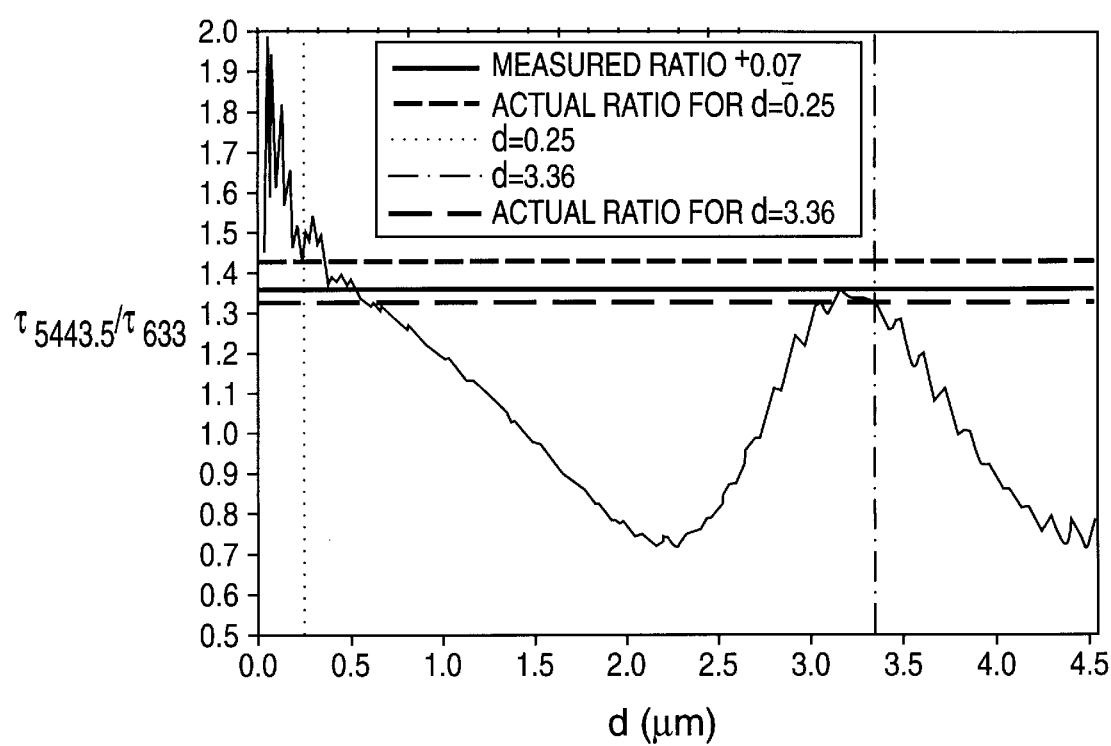

To further resolve the diameter, the ratio of τ at the two helium-neon wavelengths was used. The ratio of $\tau_{543.5}/\tau_{633} = Q_{543.3}/Q_{633}$ was used, assuming the concentration was the same for both. As shown in FIG. 6, the ratio was plotted along with the measured ratio, 1.36±0.07. The ratio for d=3.36 μm was 1.33, and for d=0.25 μm was 1.43. Both were within the experimental error, however the ratio at the larger size was much closer. The ratio oscillated about one, the asymptotic value, with all the remaining peaks smaller. This particular size remained difficult to resolve as it was the first and highest peak in FIG. 6. Other sizes, if not resolved in the first procedure, can be resolved with this second test. As seen in FIG. 6, the measured value most closely matches the larger 3.36 μm particle.

This method was used to resolve an undetermined particle size, therefore only one curve of the ratio was generated. If the size were unknown, two curves would be necessary since, for a single curve there will be more than one size that satisfies both the measured value and the theoretically generated value. Thus a third curve of the ratio of the 488 nm measurements with either the 543.5 nm or the 633 nm would be generated and the measured ratio of τ compared. The value of the diameter that is consistent for both curves is the actual diameter. This method of measuring with three wavelengths is particularly useful for smoke particles and other aerosol-type applications where the particle concentration is unknown and cannot be measured.

EXAMPLE 4

The particle sizing technique of the present invention is applicable to both mono-dispersions and poly-dispersions. "Optical Scattering Cross-Sections for Applied Dispersions of Dielectric Spheres" by Richard A. Dobbins and G. Stephen Jizmagian, Journal of the Optical Society of America, Vol. 56, Number 10, pp. 1345–1350 (October 1966), the disclosure of which is herein incorporated by reference, showed that the scattering cross section depends only weakly on the shape of the size distribution. It depends strongly on the width of the distribution. Therefore, if the width is not known, a series of curves would have to be generated from the Mie theory using various widths as input. If the approximate width is known, the distribution smooths out small oscillations like those that appear in FIGS. 4–6, making it easier to determine the particle size.

The method of the present invention works for both absorbing and non-absorbing spheres, as long as the size dispersion is not too great, such as ≦10%. Additionally, the method works for irregular shapes, with Q(x) modified from the Mie theory. Irregular particles tend to smooth the features in the curve of Q(x) in the same manner as a large size distribution does. Therefore, the Q(x) curve for irregularly shaped particles can be approximated by the curve for large size distributions. (see, for example, Bohren and Huffman, *Absorption and Scattering of Light by Small Particles*, p. 319, figure 11.20, 1983, Wiley).

The foregoing summary, description, examples and drawings of the present invention are not intended to be limiting, but are only exemplary of the inventive features which are defined in the claims.

What is claimed is:

1. A method for determining particle size by measuring optical transmission, comprising the steps of:
    calculating a ratio of the volume of solids to a total volume of particles and medium (R) of a sample solution of a solid dispersion within a medium;
    determining an optical thickness (τ) of the sample solution at one or more wavelengths;
    generating the extinction (Q) as a function of size parameter x for the one or more wavelengths; and,
    comparing a measured value of either optical thickness or volume ratio at a first wavelength to a predicted value, with the predicted value dependent on either the measured volume fraction ratio of the sample solution, or on measurement of the optical thickness between the value of about 0 to about 10.

2. The particle sizing technique of claim 1, wherein the step of calculating the ratio of solids within a first sample solution comprises measuring an amount of dilution of the solids to form the first sample solution.

3. The particle sizing technique of claim 1, wherein the step of determining the optical thickness of the sample solution comprises measuring the intensities of an electromagnetic source with and without the sample solution in a beam path of the electromagnetic source.

4. The particle sizing technique of claim 3, wherein the step of determining the optical thickness of the sample solution comprises calculating the optical thickness from the relationship of:

$$L(z)=L(0)e^{-\tau}$$

wherein L(z) and L(0) are intensities measured with a linear response photodetector, z is the optical path length in the medium, and τ is the optical thickness of the sample solution.

5. The particle sizing technique of claim 1, wherein the step of generating the extinction Q as a function of size parameter x comprises numerically generating Q(x) from a Mie code using the ratio of the refractive index of the particle divided by a refractive index of the medium as input.

6. The particle sizing technique of claim 1, further comprising the steps of:
    generating the predicted volume fraction ratio of the first sample solution;
    calculating the measured value of R of the first sample solution; and,
    determining the common values of the predicted volume fraction ratio and the measured value of R, wherein at least one determined common value represents the particle size of the solids within the sample solution.

7. The particle sizing technique of claim 6, wherein the step of generating the predicted volume fraction ratio comprises a determined value generated from the Mie theory output Q(x).

8. The particle sizing technique of claim 6, wherein the step of generating the predicted volume fraction ratio comprises a determined value generated from the Mie theory output Q(x) and the relationship of $R=2\lambda\tau x/3\pi zQ(x)$, wherein R is the predicted volume fraction occupied by the solids in the sample solution, λ is the wavelength of the radiation in the medium, τ is the optical thickness of the sample, x is size parameter, z is the optical path length, and Q is the scattering efficiency.

9. The particle sizing technique of claim 6, wherein the step of determining the common values of the predicted volume fraction ratio and the measured value of R comprises plotting R(x) as a function of x.

10. The particle sizing technique of claim 6, wherein the step of determining the common values of the predicted volume fraction ratio and the measured value of R comprises extending a constant line at the measured value of R.

11. The particle sizing technique of claim 6, wherein the step of determining the common values of the predicted volume fraction ratio and the measured value of R comprises 12. The particle sizing technique of claim 1, wherein the predicted optical thickness is calculated as a function of size parameter.

13. The particle sizing technique of claim 12, wherein the predicted optical thickness comprises a calculation from the equation:

$$\tau(x) = 3\pi z RQ(x)/2\lambda x,$$

wherein $\tau(x)$ is the predicted optical thickness, z is the optical path length, R is the volume fraction, Q is the scattering efficiency, x is equal to $\pi d/\lambda$, with d a sphere diameter, and $\lambda$ is the wavelength.

14. The particle sizing technique of claim 12, wherein the step of determining the common values of the predicted optical thickness and the measured value of $\tau$ comprises plotting $\tau(x)$ as a function of x.

15. The particle sizing technique of claim 12, wherein the step of determining the common values of the predicted optical thickness and the measured value of $\tau$ comprises extending a constant line at the measured value of $\tau$.

16. The particle sizing technique of claim 12, wherein the step of determining the common values of the predicted optical thickness and the measured value of $\tau$ comprises plotting $\tau(x)$ as a function of x and extending a constant line at the measured value of $\tau$ to correlate two common values.

17. A confirmed particle size measurement of a sample of particles of known size resulting from the use of a single wavelength comprising the method of claim 1.

18. The particle sizing technique of claim 1, further comprising the steps of:
   making an additional measurement at a second wavelength;
   converting Q(x) to Q(d) for the first and second wavelength; and,
   comparing the measured value at the first wavelength to the predicted value at the first wavelength and the measured value at the second wavelength to the predicted value at the second wavelength.

19. The particle sizing technique of claim 18, wherein the step of making an additional measurement at a second wavelength comprises adjusting the sample solution to an optical thickness equal to the determined optical thickness at the first wavelength with the addition of solid or medium to the sample.

20. The particle sizing technique of claim 18, further comprising the step of generating the predicted volume fraction ratio as a function of Q(d) for the first and second wavelength.

21. The particle sizing technique of claim 20, wherein the step of generating the predicted
   volume fraction ratio as a function of Q(d) comprises:
   converting x to d and calculating the measured value of R for the first and second wavelength; and,
   the step of comparing the measured value at the first wavelength to the predicted value at the first wavelength and the measured value at the second wavelength to the predicted value at the second wavelength comprises determining the common values of the predicted volume fraction ratio and the measured value of R for each wavelength, wherein at least one determined common value for a given d represents the particle size of the solids within the sample solution.

22. The particle sizing technique of claim 21, wherein the step of generating the predicted volume fraction ratio as a function of Q(d) comprises the equation:

$$R(d) = 2\tau d/3zQ(d),$$

wherein $\tau$ is the optical thickness, z is the optical path length, R(d) is the predicted volume fraction, Q(d) is the scattering efficiency, $\lambda$ is the wavelength in the medium, and d is the sphere diameter.

23. The particle sizing technique of claim 18, wherein the step of comparing the measured value at the first wavelength to the predicted value at the first wavelength and the measured value at the second wavelength to the predicted value at the second wavelength comprises plotting the predicted volume fraction ratio of the first and second wavelengths as functions of sphere diameter.

24. The particle sizing technique of claim 21, wherein the step of determining the common values of the predicted volume fraction ratio R(d) and the measured value of R comprises a graphic representation.

25. The particle sizing technique of claim 18, further comprising the step of generating the predicted optical thickness as a function of Q(d) for the first and second wavelength.

26. The particle sizing technique of claim 25, wherein the step of generating the predicted optical thickness as a function of Q(d) comprises the equation:

$$\tau(d) = 3zRQ(d)/2d,$$

wherein $\tau(d)$ is the optical thickness, z is the optical path length, R is the volume fraction, Q is the scattering efficiency, and d is the sphere diameter.

27. The particle sizing technique of claim 18, wherein the first sample solution is used as the second sample solution, so that the volume ratio R is the same for both measurements of $\tau$.

28. The particle sizing technique of claim 18, wherein the step of comparing the measured value at the first wavelength to the predicted value at the first wavelength and the measured value at the second wavelength to the predicted value at the second wavelength comprises plotting the predicted optical thickness of the first and second wavelengths as functions of the sphere diameter.

29. The particle sizing technique of claim 28, further comprising the step of determining the common values of the predicted optical thickness $\tau(d)$ and the measured value of $\tau$.

30. The particle sizing technique of claim 1, wherein the sample solution comprises a monodispersion.

31. A particle size measurement of a sample of particles of unknown size determined from the use of two wavelengths comprising the method of claim 18.

32. The particle sizing technique of claim 1, further comprising generating a second Q(x) from a second refractive index as an input to the Mie code when the refractive index of a particle or medium is different at a second wavelength.

33. The particle sizing technique of claim 1, further comprising generating a second Q(x) from a second medium wherein the refractive index of the two media are different.

34. The particle sizing technique of claim 1, further comprising the steps of:
   calculating the particle radius as a volume-surface mean radius.

35. The particle sizing technique of claim 34, wherein the sample solution comprises a polydispersion.

36. The particle sizing technique of claim 34, wherein the particle radius ($r_{32}$) is defined by the equation:

plotting R(x) as a function of x and extending a constant line at the measured value of R to correlate the common values.

$$r_{32} = \frac{\int_0^\infty N(r)r^3 dr}{\int_0^\infty N(r)r^2 dr}$$

wherein N(r) is the size distribution function.

37. The particle sizing technique of claim 1, wherein the scattering efficiency Q comprises a mean value $Q(r_{32})$ defined by the equation:

$$Q(r_{32}) = \frac{\int_0^\infty Q(r,m)N(r)r^2 dr}{\int_0^\infty N(r)r^2 dr}$$

wherein N(r) is the size distribution function.

38. The particle sizing technique of claim 1, comprising a ratio method using three wavelengths wherein the concentration of solids in the sample solution is unknown.

39. The particle sizing technique of claim 38, wherein the ratio method using three wavelengths comprises comparing two or more of the ratios of:

$\tau(\lambda_1)/\tau(\lambda_2) = Q(\lambda_1,d)/Q(\lambda_2,d)$;
$\tau(\lambda_1)/\tau(\lambda_3) = Q(\lambda_1,d)/Q(\lambda_3,d)$;
and $\tau(\lambda_2)/\tau(\lambda_3) = Q(\lambda_2,d)/Q(\lambda_3,d)$, wherein $\lambda_1$ is the first wavelength, $\lambda_2$ is the second wavelength, and $\lambda_3$ is the third wavelength, and $\tau(\lambda_1)$ is the optical thickness at the first wavelength, $\tau(\lambda_2)$ is the optical thickness at the second wavelength, and $\tau(\lambda_3)$ is the optical thickness at the third wavelength.

40. The particle sizing technique of claim 39, wherein two or more ratios at three wavelengths are plotted as a function of d.

41. An unknown particle size of a sample of unknown concentration determined from the use of three wavelengths comprising the method of claim 38.

42. An apparatus having a solid angle of acceptance $\theta_{1/2} \leq 5°\lambda/d$ for determining particle size by the method of claim 1.

43. A method for determining particle size by measuring optical transmission, comprising the steps of:

calculating a ratio of the volume of solids to the volume to the total volume of particles and medium (R) of a sample solution of a solid dispersion within a medium;

determining an optical thickness ($\tau$) of the sample solution at one or more wavelengths;

generating the extinction (Q) as a function of size parameter x for the one or more wavelengths; and, comparing a measured value of either optical thickness or volume ratio at a first wavelength to a predicted value, with the predicted value dependent on either the measured volume fraction ratio of the sample solution, or on measurement of the optical thickness between the value of about 0 to about 10;

wherein the step of calculating the ratio of solids within a first sample solution comprises measuring an amount of dilution of the solids to form the first sample solution;

wherein the step of calculating the measured value of R comprises the relationship of $R = s/\delta$, with a measured value of $\tau$, wherein R is the volume fraction occupied by the solids in the sample solution, s is the fraction of solids, and $\delta$ is a density of the particles.

\* \* \* \* \*